United States Patent [19]
Johnson et al.

[11] Patent Number: 5,322,500
[45] Date of Patent: Jun. 21, 1994

[54] VARIABLE RATIO BLOOD-ADDITIVE SOLUTION DEVICE AND DELIVERY SYSTEM

[75] Inventors: Gilbert H. Johnson; Stephen R. Straus; Joseph D. Giordano, all of Las Vegas, Nev.

[73] Assignee: Cardio Pulmonary Supplies, Inc., Las Vegas, Nev.

[21] Appl. No.: 26,277

[22] Filed: Mar. 4, 1993

Related U.S. Application Data

[63] Continuation of Ser. No. 697,666, May 9, 1991, abandoned.

[51] Int. Cl.$^5$ .............. A61M 37/00; A61M 1/00; A61M 31/00; A61F 7/12
[52] U.S. Cl. .................... 604/4; 604/30; 604/56; 604/65; 604/67; 604/82; 604/83; 604/113; 604/131; 604/207; 128/DIG. 12; 128/DIG. 13
[58] Field of Search ............ 128/DIG. 6, 12, 13; 604/4, 7, 21, 27, 30-31, 43, 56, 65-67, 81-83, 113, 131, 141, 143, 151, 207, 246

[56] References Cited

U.S. PATENT DOCUMENTS

| | | | |
|---|---|---|---|
| 2,481,496 | 9/1949 | Brewer | 137/101.19 |
| 4,416,280 | 11/1983 | Carpenter et al. | 604/4 |
| 4,432,754 | 2/1984 | Urquhart et al. | 604/56 |
| 4,625,494 | 12/1986 | Iwatschenko et al. | 604/82 |
| 4,738,541 | 4/1988 | Weber | 137/101.19 |
| 4,747,826 | 5/1988 | Sassano | 604/113 |
| 4,769,001 | 9/1988 | Prince | 128/DIG. 13 |
| 4,778,449 | 10/1988 | Weber et al. | 604/65 |
| 4,874,359 | 10/1989 | White et al. | 128/DIG. 13 |
| 5,029,584 | 7/1991 | Smith | 604/28 |
| 5,059,173 | 10/1991 | Sacco | 604/80 |

*Primary Examiner*—Randall L. Green
*Assistant Examiner*—P. Zuttarelli
*Attorney, Agent, or Firm*—James E. Brunton

[57] ABSTRACT

A variable ratio, blood-additive solution, mixing device and delivery system that permits the varying of the ratio of blood to solution from either all blood to pure solution and any ratio of the two, either continuously or intermittently, prior to or during cardiovascular and cardiac perfusion procedures, particularly warm or cold cardioplegia procedures for open heart surgery.

20 Claims, 3 Drawing Sheets

VARIABLE RATIO BLOOD-ADDITIVE SOLUTION DEVICE AND DELIVERY SYSTEM

This application is a continuation of application Ser. No. 07/697,666, filed May 9, 1991, now abandoned.

BACKGROUND OF THE INVENTION

The present invention relates to a device and system for delivering on command any ratio of blood to blood-additive solution of a blood/solution mixture during cardio vascular and cardiac perfusion procedures and more particularly to intermittently and/or continuously delivering on command any ratio of blood to cardioplegia solution of a blood/cardioplegia mixture during cardiac or "open heart" surgery.

Generally, cardioplegia is used in conjunction with hypothermia. This technique is commonly called cold cardioplegia. Based on the preference of the cardiac surgical team, a crystalloid chemical solution or some mixture of the solution and blood mixture is intermittently or continuously perfused to arrest the heart. For example, using cold cardioplegia, the heart is reperfused approximately every twenty minutes to keep the heart arrested.

Recently, open heart surgeons are utilizing a new technique called warm continuous blood cardioplegia. This technique does not use hypothermia, rather, it continually uses a cardioplegia mixture of warm (approximately 37 degrees centigrade) oxygenated blood and solution mixture throughout the cardiac surgery. See The Perfusionist's Perspective of Warm Continuous Blood Cardioplegia: A New Technique of Myocardial Protection, A. Karim Jabr, C.P., and Antony Panos, M.D., Proceeding of the American Academy of Cardiovascular Perfusion, Vol. 10, Aug. 1989. This technique appears to be safe and effective in prolonging high risk procedures, prolonging operative time, substantially eliminating the period of ischemia, limiting the period and injury of reperfusion, attaining exceptional myocardial preservation, and abolishing the detrimental effects of hypothermia.

Generically, these methods fall under the general category of myocardial protection techniques. Whether the blood cardioplegia is warm or cold blood, or intermittently and continuous, the blood and solution mixture is predetermined, typically in a 4 to 1 ratio, blood to solution. Presently, the ratio of blood to solution is pre-operatively fixed by the diameter of the tubing transferring the blood (typically ¼ inch diameter tubing) and the solution (typically 1/16 or ⅛ inch diameter tubing). Thus, the ratio is fixed throughout the operation. This manner of delivering the blood and solution can cause certain complications during the operation. In addition, the fixed ratio may cause certain complications on a patient by patient basis, during the operation.

For instance, simultaneously using tubings of different diameter in the same pump head can unfortunately cause bunching of the tubing or inappropriate occlusion of both the ¼-inch and the 1/16-inch line. Obviously, bunching of the tubing could lead to adverse consequences for the patient as a result of the time that it takes the perfusionist or physician to correct the problem. In addition, changing the bunched tubing during the operation increases the chance of line contamination or air getting into the system. Hence, a single tube is desirable.

Further, the typically used ratios of blood to solution, e.g. 4:1 and 2:1, that are pre-operatively fixed, may not necessarily be the optimal ratio for the patient, either when initially perfusing the heart or reperfusing the heart to keep it arrested during the operation. In addition, delivering a fixed ratio of blood/solution mixture with warm cardioplegia, the heart is continually perfused with solution that is mostly composed of water, causing tissue cells to swell. When the heart is revived, non-blood fluids in the tissue or lungs cause the heart to work harder, thereby straining the heart and prolonging recovery. Moreover, some heart surgery teams do not use a blood/solution mixture rather they perfuse the heart with pure solution. Whatever the preference may be, increasing the solution delivered to the heart using the present systems increases the total volume of fluid delivered to the heart and correspondingly varies the pressure on the aortic valve. Variation of the pressure on the aortic valve may affect the competency of the valve and may cause distension. Thus, it is desirable to control the amount of solution and/or vary the blood/solution ratio to customize the blood/solution mixture for each patient and to adjust this ratio during the operation or, if preferred, to intermittently deliver pure solution as necessary.

It would be highly advantageous therefore, to remedy the foregoing and other deficiencies and inherent limitations associated with the delivery of a blood/blood-additive solution mixture of a pre-determined ratio during cardio vascular and cardiac perfusion procedures.

Accordingly, it is a principal object of the device and system of the present invention to provide a device and system to selectively vary the ratio of blood to blood-additive solution from either all blood to pure solution and any ratio of the two, either continuously or intermittently, throughout the cardio vascular and cardiac perfusion procedure or surgery.

It is a object of the device and system of the present invention to provide a device and system that requires a single tube blood-additive solution pumping arrangement to deliver the blood and/or solution to the perfusion site.

It is a further object of the device and system of the present invention to vary the ratio of blood to solution without changing the total volume and maintaining a consistent pump flow rate and aortic pressure.

It is an advantage of device and system of the present invention to be utilized in either warm or cold cardioplegia.

It is a further advantage of the device and system of the present invention to permit the perfusionist to use either a single tube or double tube, blood-additive solution pumping arrangement.

It is a further advantage of the device and system of the present invention to permit the perfusionist to use the device and system for all types of adult and pediatric cardiac surgery, including, coronary artery bypass surgery, valvular surgery, and other vascular valve surgery requiring cardioplegia.

It is a further advantage of the device and system of the present invention to minimize the delivery of excess solution whereby less water, or other non-blood fluids, is absorbed by the tissues and lungs, reducing post-operative heart strain, thereby shortening the recovery period.

It is a further advantage of the device and system of the present invention to instantaneously select a desired ratio of blood to solution without changing the tubing of certain diameters to tubing different diameter.

The foregoing and more specific objects advantages and features of the present invention will become readily apparent to those skilled in the art from the following detailed description of the preferred embodiment thereof taken in conjunction with the drawings.

BRIEF SUMMARY OF THE INVENTION

The device in the system of the present invention varies the ratio of blood to blood-additive solution in a blood/solution mixture from either all blood to pure solution in any ratio of the two, either continuously or intermittently. The device of the present invention comprises a solution conduit, a blood conduit and a mixing coupler having a solution inlet, a blood inlet and a blood/solution mixture outlet. The solution conduit is connected to the solution inlet and the blood conduit is connected to the blood inlet. A blood/solution conduit is connected to the blood/solution outlet. The blood/solution conduit has an outlet adapted to connect to a site of perfusion. A fluid regulating means for selectively controlling the flow of solution, such as a valve, is in the solution conduit. The device of the invention may further comprise, a one-way valve, located between the regulating means and the solution inlet, that prohibits fluid flow from the solution inlet. The device of the invention may further comprise a second fluid regulating means for selectively controlling or stopping the flow of blood, located in the blood conduit, and instead of or in addition to the solution regulating means. The device may further comprise a means for continuously and instantaneously monitoring and displaying the ratio of blood to solution of the blood/solution mixture. The monitoring and displaying means comprise a plurality of fluid flow measuring means in at least two of the blood conduit, solution conduit or blood/solution conduit, and a computer to calculate the ratio of blood to solution based upon the measurements from at least two fluid flow measuring means. Each fluid flow measuring means are adapted to provide an electronic signal corresponding to the instantaneous fluid flow. In an alternative embodiment of the device invention, the monitoring and displaying means comprise two pressure measuring means and a means for measuring the instantaneous volume of blood/solution mixture delivered to the perfusion site. In the alternative embodiment, one pressure measuring means is located at the source of the solution and the other pressure measuring means is located near the connection of the solution conduit and solution inlet. The computer means calculates the ratio of blood to solution based upon the measurements of the pressure measuring means, the known density of the blood-additive solution, the distance between the points of measurement, the area of the solution conduit, and the measured instantaneous volume of blood/solution delivered to the site of perfusion.

The system invention comprises either aforementioned device invention, a plurality of solution sources connected to the device invention, an oxygenated blood source connected to the device invention, a blood pump drawing the oxygenated blood from the source to the device invention, and a blood/solution pump drawing the blood/solution mixture from the device to the site of the perfusion. For the system invention comprising the alternative device invention, the blood/solution pump is retrofitted with the blood/solution volume measuring means which comprises an angular rotation sensing means and angular rotation indicators on the pump head of the blood/solution pump. The blood/solution volume measuring means is adapted to provide an electronic signal corresponding to the angular distance travelled by the pump head to the monitor and displaying means. The computer means calculates the instantaneous blood/solution volume delivered based upon the measurement of the blood/solution volume measuring means and the known volume delivered by the pump at a known rotation rate of the pump head. As previously described, the computer means calculates the ratio of the blood to solution of the blood/solution mixture delivered to the perfusion site.

BRIEF DESCRIPTION OF THE DRAWINGS

Drawings accompanying the disclosure and the various views thereof may be briefly described as.

DETAILED DESCRIPTION OF THE PREFERRED EMBODIMENTS

Figure 1:
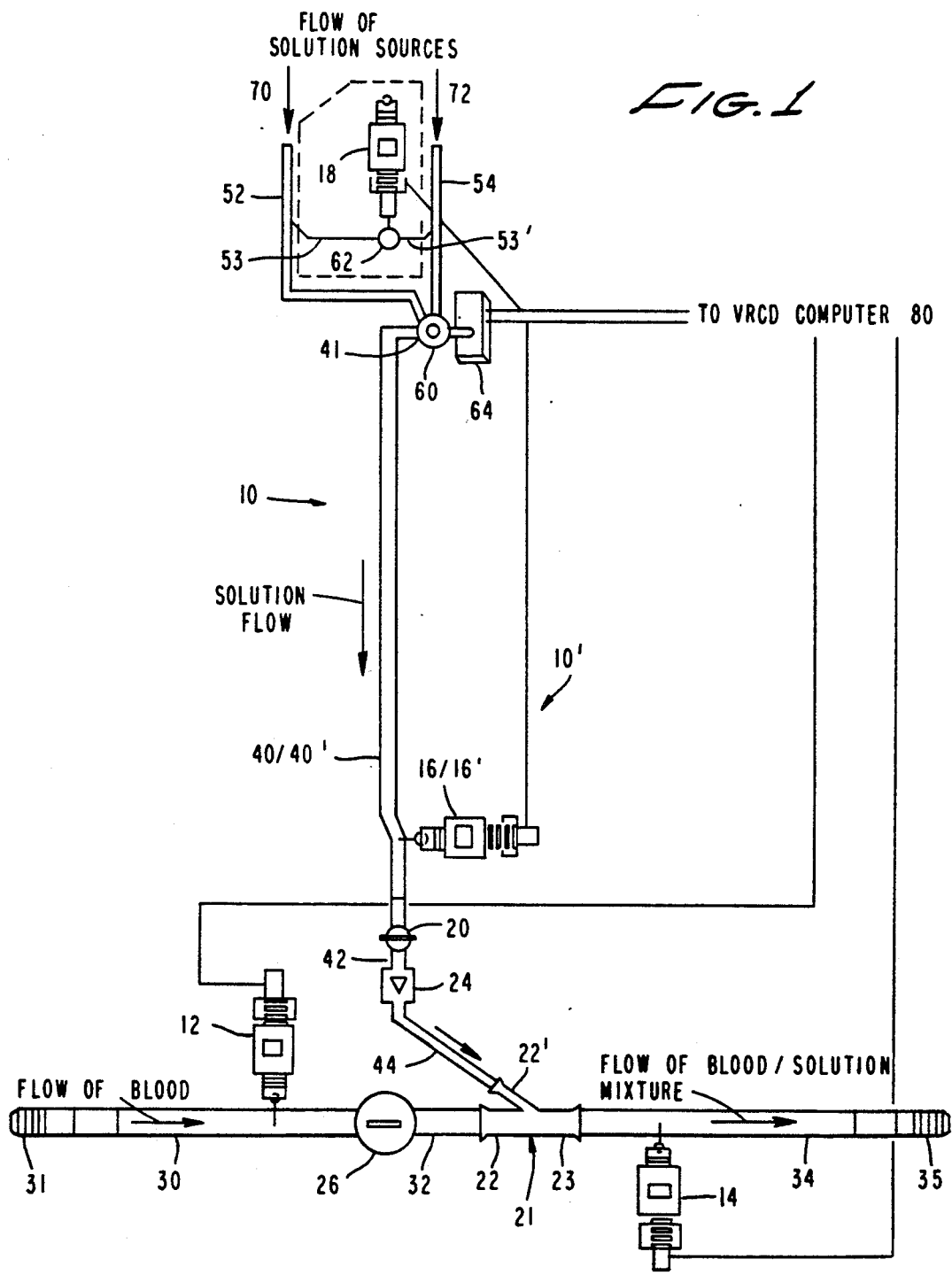
FIG. 1: A generalized view of the device invention.

The Variable ratio, blood-additive solution, mixing device 10 of the present invention is shown generally in FIG. 1. The device 10 comprises a solution conduit 40 through which a blood-additive solution, such as cardioplegia or potassium solution, flows. The solution conduit 40 having an inlet 41 connected to a source selecting means 60 for selecting one solution source from a plurality of solution sources, such as solution sources 70 and 72. The selecting means 60 has a plurality of inlets, one for each solution source. Each solution source is connected to the selecting means 60 by a solution source conduit. In FIG. 1, solution conduit 52 connects the selecting means 60 to solution source 70 and solution conduit 54 and connects selecting means 60 to solution source 72. In an alternative embodiment of the device invention, the selecting means 60 is a three-way valve that is adapted such that its setting is read by a sensor 64. The sensor 64 conveys the position of the selecting means 60, i.e. which source is providing the solution flow, by means of an electronic signal to the computer 80.

The outlet of the solution conduit 40 is connected to a variable valve 20. The variable valve regulates and controls the rate of flow of solution. A further solution conduit 42 connects the outlet of the variable valve 20 to the inlet of a one-way valve 24. The purpose of the one-way valve 24 is discussed below. Generally, the one-way valve 24 permits the flow of solution in one direction and prohibits the flow of any fluid, e.g. solution, blood, or blood/solution mixture, from backing up into the solution sources.

A blood conduit 30 has an inlet 31 connected to a source of blood, preferably oxygenated blood. The outlet of the blood conduit 30 is connected to a butterfly valve 26. In the preferred embodiment, the butterfly valve 26 either permits the full flow of blood or stops the flow of blood. In an alternative embodiment of the device invention, the butterfly valve 26 can be used to regulate the flow of blood like the variable valve 20 regulates the flow of solution. In the alternative embodiment, the butterfly valve 26 can be used instead of the variable valve 20 or in addition t it.

FIG. 1 also shows a Y-connector 21 having a blood inlet 22, a solution inlet 22' and a blood/solution mixture outlet 23. The blood inlet 22 is connected to the outlet of the butterfly valve 26 by a blood conduit 32. The solution inlet 22' is connected to the outlet of the one-way valve 24 by a solution conduit 44. As indicated in FIG. 1, the solution flows under the force of gravity from the source, 70 (or 72), through the solution conduits 52 (or 54) and 40, the variable valve 20, the solution conduit 42, the one-way valve 24, and solution conduit 44. The flow of solution then enters the solution inlet 22' of the Y-connector 21 and the flow of blood enters the blood inlet 22, thereby causing the solution and blood to mix in the Y-connector 21 and exit the Y-connector 21 through its blood/solution mixture outlet 23. The outlet 23 is connected to a blood/solution mixture conduit 34. The outlet 35 of the conduit 34 is adapted to direct the blood/solution mixture to the site of perfusion, i.e. the coronary arteries of a patient's heart undergoing cardiac surgery. The site of perfusion, however, may also be another organ or member of a patient's body, not necessarily undergoing a surgical operation, or an experimental site in a controlled laboratory setting.

In the preferred embodiment of the device invention 10, as shown in FIG. 1, the variable valve 20 in regulating the flow of solution also regulates the ratio of blood to solution in the blood/solution mixture. A physician or perfusionist can thus continuously or intermittently select any desired ratio of blood to solution and selectively vary the ratio on command during the course of perfusion, or more particularly at any time during a cardiac surgery. The device invention of the preferred embodiment can be utilized with either cold or warm cardioplegia and can be utilized in any cardiovascular surgery that includes perfusion, especially perfusion of a blood-additive solution, such as cardioplegia. Further, a physician may deliver pure crystalloid to the perfusion site by turning the butterfly valve 26 to the off position, thereby stopping the flow of blood. The physician may also direct pure oxygenated blood to the perfused site by turning the variable valve completely off, thereby stopping the flow of solution into the Y-connector 21.

FIG. 1 further shows means for continuously monitoring the ratio of blood to solution of the blood/solution mixture. At least two of the blood flow measuring means 12, the solution flow measuring means 16, and the blood/solution mixture flow means 14 are used to continuously measure the instantaneous flow rate or volume delivered of blood, solution, and blood/solution mixture, respectively. Each of the aforementioned means are in-line measuring means, that is, each measures the fluid flow in the respective fluid conduit.

Generally, the flow measuring means may be placed anywhere along the fluid conduit. With respect to blood flow measuring means 12, it could be placed generally between the inlet of the blood conduit 30 and the outlet of blood conduit 32. Regarding the solution flow measuring means 16, it could be located between the inlet of solution conduit 40 and the outlet of solution conduit 44. Concerning the blood/solution mixture flow measuring means 14, it could be located between the inlet and outlet of blood/solution mixture conduit 34. As will be described with respect to the variable ratio blood-additive solution delivery system of the present invention, placement of the flow measuring means will be further specified.

Each flow measuring means 12, 14, and 16 are adapted to provide a electronic signal corresponding to the rate of flow of the fluid. Further, each flow measuring means is electronically connected to the variable ratio cardioplegia device (VRCD) computer 80. The VRCD computer 80 is programmed such that it calculates the ratio of blood to solution of the blood/solution mixture. At least two different flow measurements are necessary in order to determine the ratio. All three of the flow measuring means are not necessary and variations of the preferred embodiment may include flow measurements from any permutation of the flow measuring means 12, 14 and 16. In order to calculate the ratio, however, the solution flow rate and blood flow rate, or the solution flow rate and blood/mixture flow rate, or the blood flow rate and blood/solution flow rate, must be measured. For example, if the solution flow rate and blood flow rate are measured, the ratio is the blood flow rate divided by the solution flow rate. If the solution flow rate and blood mixture flow rate are measured, the ratio is the difference between the blood/solution mixture flow rate and the solution flow rate divided by the solution flow rate. And if the blood flow rate and blood/solution mixture flow rate are measured, the ratio is the blood flow rate divided by the difference between the solution/blood mixture flow rate and the solution flow rate.

As will be described below, the VRCD computer 80 may further comprise a means to display the ratio of blood to solution and the flow rate or volume delivered of blood, solution and blood/solution mixture. Since the flow rate measuring means 12, 14 and 16 continuously measure the instantaneous flow of blood, solution, blood/solution mixture, respectively, and are electronically connected to the computer 80 having a display, the physician or perfusionist can monitor the ratio and select a desired ratio by manipulating the variable valve 20 (and/or the butterfly valve 26) and reading the ratio from the computer display. An alternative preferred embodiment of the device invention 10' utilizes pressure measuring means 18 and 16' instead of flow measuring means 12, 14 and 16. This embodiment will be more further discussed in the following detailed description of the variable ratio, blood-additive solution delivery system.

Figure 2:
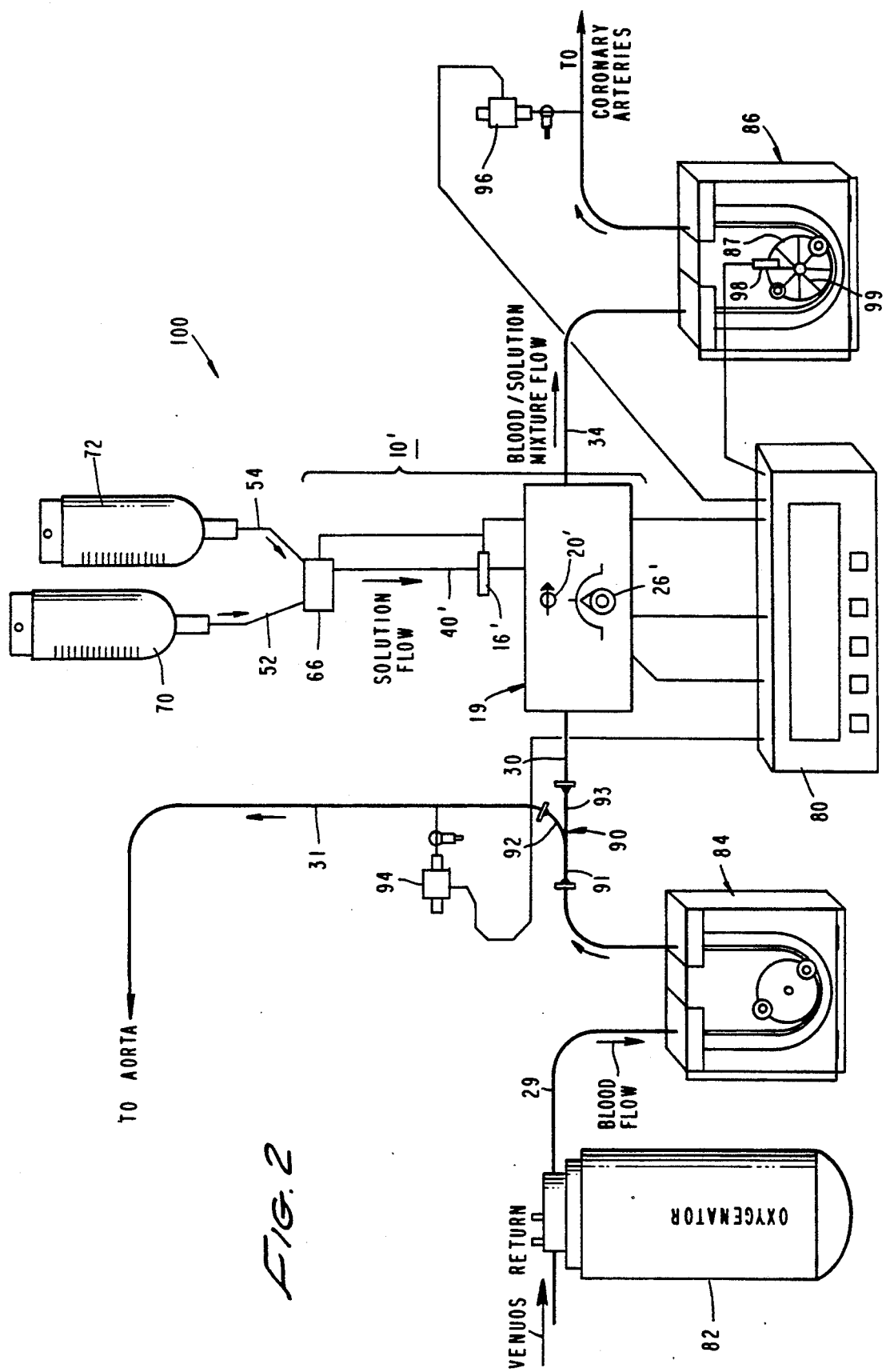
FIG. 2: A generalized view of the system invention.

The variable ratio, blood-additive solution delivery system 100 of the present invention is shown generally in FIG. 2. The system 100 comprises a plurality of blood-additive solution sources, e.g. 70 and 72, such as cardioplegia. The system invention further comprises the device 10'. The device 10' is connected to the solution sources 70 and 72 by solution conduits 52 and 54 respectively. The black box 66 includes the first pressure measuring means 18, the source selecting means 60, the pressure selecting means 62 and the source selecting means sensor 64, shown in FIG. 1. The pressure measuring means 18 is in-line with the solution conduits 52 and 54 via pressure sensor means 53 and 53', respectively. The pressure selecting means 62 selects the solution source whose pressure is being measured by the first pressure means 18. The first pressure measuring means 18 is adapted to provide an electronic signal corresponding to the solution pressure to the VRCD computer 80.

The device 10' further comprises an acceleration manifold 40' connecting the outlet of source switching means 60 to the input of variable valve 20. The acceleration manifold 40' is a conduit for the flow of solution flowing under the force of gravity from the solution source to the variable valve 20. Near the connection of the acceleration manifold 40' and the variable valve 20 is a second pressure measuring means 16' that is in-line with the acceleration manifold 40'. This second pressure measuring means is also adapted to provide an electronic signal corresponding to the pressure at that point to the VRCD computer 80. The rectangular box 19 includes the blood conduit 30, the blood conduits 30 and 32, the butterfly valve 26, the Y-connector 21, the solution conduits 42 and 44, the variable valve 20, the one-way valve 24 and the inlet portion of blood/solution mixture conduit 34. The rectangular box 19 also has variable valve control knob 20' and butterfly control knob 26'.

As further shown in FIG. 2, the blood/solution mixture conduit 34 extends through a blood/solution mixture pump 86. The pump 86 draws the blood/solution mixture from the outlet of the Y-connector 21 through the blood/solution conduit 34 to the coronary arteries of the patient's heart. Pump 86 is adapted or retrofitted with a rotation sensing means 98 for determining the angular distance travelled by the rotating pump head 87. The rotation sensing means 98 can be an optical code reader or a electromagnetic detector. The encoder markings 99 on the pump head 87 can correspondingly be either optical indicators or metal or magnetic contacts. The more discreet the rotational indicators 99, the more accurate the rotational sensor will be able to determine the angular distance travelled by the pump head 87. The rotation sensing means 98 is adapted to provide an electronic signal corresponding to the angular distance to the VRCD computer 80. Using the manufacturer's specifications that set forth the volume output of the pump 86 at a particular pump head rotation rate, the VRCD computer 80 can be programmed to calculate the instantaneous flow rate of the blood/solution mixture leaving the pump 86 through the conduit 34.

As further shown in FIG. 2, the system invention of the preferred embodiment further comprises a split connector 90 having an inlet 91, a first outlet 92 and a second outlet 93. The second outlet 93 is connected to the inlet of the blood conduit 30. The outlet 91 is connected to a blood conduit 29 connected to a blood oxygenator 82. The blood conduit 29 runs from the oxygenator 82 through a blood pump 84. The pump 84 draws the oxygenated blood from the oxygenator 82 and drives the oxygenated blood through the blood conduit 29 to the split connector 90 where a portion of the oxygenated blood is delivered via the blood conduit 30 to the device invention 10'. Another portion of the oxygenated blood is sent to the aorta of the patient's heart through a blood conduit 31 having an inlet connected to the outlet 92 and an outlet adapted to deliver blood to the aorta.

The VRCD computer 80 has inputs to accept the electronic signals from the first pressure measuring means 18, the second pressure measuring means 16' and the rotational sensor 98. The computer 80 is programmed to calculate the instantaneous solution volume delivered by using the measured pressures at the solution source 70 or 72 and near the bottom of the acceleration manifold 40', according to the Bernoulli equation:

$$Y_1 + \frac{P_1}{\rho} + \frac{V_1^2}{2G} = Y_2 + \frac{P_2}{\rho} + \frac{V_2^2}{2G} \quad (1)$$

Figure 3:
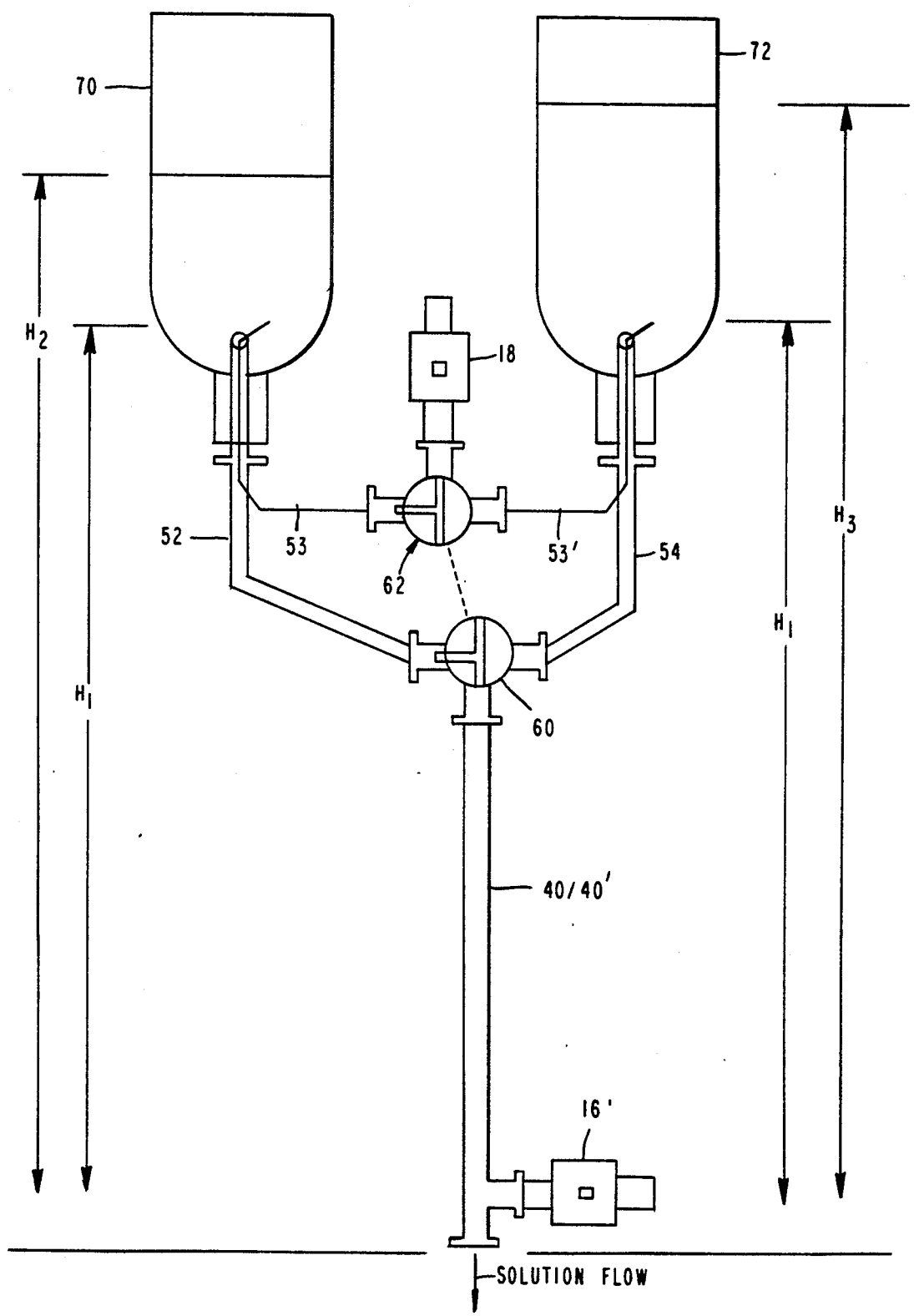
FIG. 3: A more detailed view of a portion of an alternative embodiment of the device invention.

Referring to FIG. 3, taking the reference point 1 at the second pressure measuring means 16' and the second point 2 at the solution source 70 or 72, $Y_2 - Y_1 = H_1$, the height of point 2 with respect to point 1. Further, since the area of the solution source 70 or 72 is much greater than the area of the solution conduit, 52 or 54, respectively, the velocity at point 2 is negligible. Thus $V_2$ approximately equals zero. Equation 1 thus simplifies to:

$$H_1 + \frac{P_1}{\rho} + \frac{V_1^2}{2G} = \frac{P_2}{\rho} \quad (2)$$

where $\rho$ is the density of the solution (which is approximately 1 for cardioplegia) and G is the force due to gravity ($-9.8$ meters per second squared) $V_1$ is the unknown solution velocity at point 1, $P_1$ is the pressure at point 1 and $P_2$ is the pressure at point 2. Equation 2 can be solved for $V_1$ as follows:

$$V_1 = \sqrt{2G\left(\frac{P_2 - P_1}{\rho} - H_1\right)} \quad (3)$$

Using Equation No. 3, the instantaneous volume flowing through a solution conduit of radius R can be calculated by multiplying the fluid velocity by the tube area, $\pi R^2$. Multiplying Equation No. 3 by $\pi R^2$ the instantaneous solution flow can be calculated as follows:

$\pi R^2 V_1 =$ the instantaneous solution volume delivered (flow)

Since the radius of the blood conduit 52 and 54 and 40' (40' is known, as well as the height $H_1$ (approximately 1 meter) and density of the solution are fixed and constant. The instantaneous solution flow can be calculated by taking the difference between the measured pressure at point 2 and at point 1. It is worth noting that a change in the fluid level $H_1$ or $H_2$ of the solution sources 70 and 72, respectively, will equally affect the pressure at point 1 and point 2, thereby canceling the effects of the drop in fluid level $H_1$ or $H_2$. Thus, the instantaneous fluid flow is not affected by the fullness of the solution source.

The computer 80 calculates by discreet time integration the total solution volume delivered from the selected solution source, 70 or 72. Further, the computer 80 calculates the blood/solution mixture volume as previously described. Using the calculated instantaneous solution volume delivered and the calculated instantaneous blood/solution mixture delivered, the computer 80 calculates the blood to solution ratio of the blood/solution mixture by dividing the difference between the blood/solution volume delivered and the instantaneous solution volume delivered by the instantaneous blood/solution volume delivered.

The VRCD computer 80 of the system invention depicted in FIG. 2 has a means for displaying the ratio of blood to solution, as well as, optional means for displaying other related and important parameters, such as the coronary sinus pressure measured by the pressure measuring means 96 and/or the perfusion pressure in the blood conduit 31 measured by the pressure measuring means 94. Both pressure measuring means 94 and 96 are in-line and adapted to provide an electronic signal corresponding to the measured pressure to the VRCD computer 80.

An alternative embodiment of the system invention 100 replaces the device invention 10' with the device invention 10. In that case, rotational sensor 98 and rotational markings 99 are not necessary. In addition, pressure measuring means 16' and 18 are not used, rather at least two of the flow measuring means 12, 14 and 16 are used. In the alternative embodiment of the system invention 100' (not shown), the blood flow measuring means 12 is more specifically located in-line with blood conduit 30 between the output 93 of the split connector and the inlet 22 of the Y-connector. Further, the blood/solution mixture flow measuring means 14 in-line with blood/solution mixture conduit 34 is more specifically located between the outlet 23 of the Y-connector and the pump 86.

Although the number, dimensions and volume and pressure outputs of the device invention and system invention are not critical, in one operative embodiment of the device and system invention, the blood and blood/solution mixture conduits are tubular conduits having a ¼ inch inner diameter and the solution conduits are tubular conduits having a 1/16 inch inner diameter. Further, the flow rate of the pump 86 is 50 to 500 milliliters per minute, the flow rate of solution from the solution sources is 5-10 milliliters per minute to 100-250 milliliters per minute. In addition, the pressure of blood conduit 31 delivering oxygenated blood to the aorta is approximately 100 mmHg. The pressure measuring means 16' and 18 are COBE or ABBOTT pressure monitoring transducers and the flow measuring means 12, 14 and 16 are flow turbine meters. Other suitable components may be substituted for these components without substantially departing from the spirit of this invention. Further, various modifications and additions may be made and will be apparent to those skilled in the art. Accordingly, the invention should not be limited by the foregoing description, but rather should be defined only by the following claims.

What is claimed is:

1. A device for mixing a solution with blood to form a mixture and for delivering the mixture to a site of perfusion, said device comprising:
   a. a source of blood and a source of solution;
   b. a mixing means interconnected with said source of blood and said source of solution for mixing the blood and the solution to form a mixture, said mixing means having a plurality of inlets and a dispensing means for delivering said mixture to the site of perfusion;
   c. a first path means interconnecting said source of blood and said mixing means for defining a blood flow path between said source of blood and one of said inlets of said mixing means;
   d. a second path means interconnecting said source of solution and said mixing means for defining a solution flow path between said source of solution and one of said inlets of said mixing means;
   e. a third path means interconnected to said dispensing means for delivering said mixture to the site of perfusion for defining a mixture flow path between said dispensing means and the site of perfusion;
   f. a first pump disposed in said first path means for moving the blood along said first path means;
   g. a second pump disposed in said third path means for moving said mixture along said third path means;
   h. varying means in communication with said source of blood and said source of solution for selectively varying a ratio of blood to solution in said mixture;
   i. monitoring means in communication with said mixing means for continuously and instantaneously monitoring the ratio of blood to solution in said mixture, said monitoring means comprising:
      (a) computer means for calculating the ratio of blood to solution in said mixture;
      (b) pressure measuring means connected to said third path means for continuously measuring an instantaneous pressure of said mixture in said third path means, said pressure measuring means being adapted to provide an electronic signal to said computer means representing the pressure in said third path means; and
      (c) flow measuring means disposed in at least two of said first, second and third path means for determining an instantaneous rate of fluid flow therethrough, said flow measuring means being adapted to provide an electronic signal to said computer means representing the rate of fluid flow determined; and
   j. means in communication with said first path means for diverting along a fourth flow path leading to the site of perfusion a portion of blood flowing in said first path means.

2. The mixing device as defined in claim 1 in which said varying means comprises a fluid regulating means for selectively controlling the fluid flow.

3. The mixing device as defined in claim 1 in which said solution comprises cardioplegia.

4. The mixing device as defined in claim 1 further comprising an oxygenator disposed in said second path means.

5. A variable ratio mixing device for dispensing a mixture of blood and solution toward a site of perfusion, said device comprising:
   a. a source of blood and a source of solution;
   b. a mixing means interconnected with said source of blood and said source of solution for mixing blood and solution, said mixing means having a plurality of inlets and including dispensing means for dispensing a mixture of blood and solution;
   c. a first path means interconnecting said source of blood and said mixing means for defining a blood path between said source of blood and one of said inlets of said mixing means;
   d. a second path means interconnecting said source of solution and said mixing means for defining a solution path between said source of solution and one of said inlets of said mixing means;
   e. a third path means interconnected to said dispensing means for delivering said mixture to the site of perfusion for defining a blood and solution mixture path between said dispensing means and the site of perfusion;
   f. a first pump disposed in said first path means for moving said blood along said first path means;
   g. a second pump disposed in said third path means for moving said mixture of blood and solution along said third path means;

h. varying means in communication with said source of blood and said source of solution for selectively varying a ratio of blood to solution in said mixture of blood and solution;

i. monitoring means in communication with said mixing means for continuously and instantaneously monitoring the ratio of blood to solution in said mixture of blood and solution, said monitoring means comprising:

(a) a computer means having:
   (i) a plurality of input means for receiving electronic signals;
   (ii) means for calculating the ratio of blood to solution based on said electronic signals; and
   (iii) display means for displaying said ratio;

(b) a plurality of flow measuring means for determining an instantaneous ratio of fluid flow, each of said flow measuring means being adapted to generate and transmit to said computer means an electronic signal representative of the rate of fluid flow, said flow measuring means being disposed in at least any two of said first path means, said second path means and said third path means; and j. a means in communication with said first path means for diverting a portion of the blood flow from said first path means along a fourth path means to the site of perfusion.

6. The mixing device as defined in claim 5 further comprising pressure measuring means for continuously measuring a pressure of blood flow in said fourth path means, said pressure measuring means being adapted to generate and transmit to said computer means an electronic signal representative of the pressure of blood flow in said fourth path means.

7. The mixing device as defined in claim 6, where said solution is cardioplegia.

8. The mixing device as defined in claim 6, further comprising an oxygenator disposed in said second path means.

9. The mixing device as defined in claim 8, further comprising a heat exchanger, disposed in said third path means.

10. A variable ratio mixing device for mixing blood and solution and for dispensing the mixture thereof toward a site of perfusion, said device comprising:
   a. a source of blood and a source of solution;
   b. a mixing means in communication with said source of blood and said source of solution for mixing blood and solution to form a mixture, said mixing means having first and second inlets and an outlet, said first inlet being connected to said source of blood and said second inlet being connected to said source of solution;
   c. dispensing means connected to said outlet of said mixing means for dispensing said mixture toward the site of perfusion; and
   d. monitoring means in communication with said mixing means for continuously and instantaneously monitoring a ratio of blood to solution in said mixture, said monitoring means comprising flow measuring means for determining an instantaneous rate of fluid flow of at least two of the fluid flows comprising blood flowing toward said mixing means, solution flowing toward said mixing means and mixture flowing toward the site of perfusion.

11. The mixing device as define din claim 10 in which said flow measuring means is adapted to generate and transmit electronic signals corresponding to the rates of fluid flow determined and in which said monitoring means further comprises computer means for receiving said electronic signals generated by said flow measuring means and for calculating the ratio of blood to solution in said mixture.

12. The mixing device as defined in claim 11 further including pressure measuring means disposed intermediate said mixing means and the site of perfusion for continuously measuring an instantaneous pressure of said mixture flowing toward the site of infusion, said pressure measuring means being adapted to provide an electronic signal to said computer means representing the pressure determined thereby.

13. The mixing device as defined in claim 11 further including means for diverting to the site of perfusion a portion of the blood flowing from said source of blood to said mixing means.

14. A variable ratio mixing device for mixing blood and solution and for dispensing the mixture thereof toward a site of perfusion, said device comprising:
   a. a source of blood and a source of solution;
   b. a mixing means interconnected with said source of blood and said source of solution for mixing blood and solution to form a mixture, said mixing means having first and second inlets and an outlet, said first inlet being connected to said source of blood and said second inlet being connected to said source of solution;
   c. dispensing means connected to said outlet for dispensing said mixture toward the site of perfusion;
   d. a first pump disposed intermediate said source of blood and said mixing means for moving said blood toward said mixing means;
   e. a second pump disposed intermediate said mixing means and the site of perfusion for moving said mixture toward the site of perfusion;
   f. varying means in communication with said source of blood and said source of solution for selectively varying a ratio of blood to solution in said mixture;
   g. monitoring means in communication with said mixing means for continuously and instantaneously monitoring the ratio of blood to solution in said mixture, said monitoring means comprising:
      (i) flow measuring means for determining an instantaneous rate of fluid flow of at least two of fluid flows comprising blood flowing toward said mixing means, solution flowing toward said mixing means and mixture flowing toward the site of perfusion, said flow measuring means being adapted to generate said transmit electronic signals corresponding to the rates of fluid flow determined; and
      (ii) computer means for receiving said electronic signals generated by said flow measuring means and for calculating the ratio of blood to solution in said mixture.

15. The mixing device as defined in claim 14 further including pressure measuring means disposed intermediate said mixing means and the site of perfusion for continuously measuring an instantaneous pressure of said mixing flowing toward the site of infusion, said pressure measuring means being adapted to provide an electronic signal to said computer means representing the pressure determined thereby.

16. The mixing device as defined in claim 14 further including means for diverting to the site of perfusion a portion of the blood flowing from said source of blood to said mixing means.

17. The mixing device as defined in claim 14 further including one way valve means disposed between said source of solution and said mixing means for permitting solution flow only in a direction toward said mixing means.

18. The mixing device as defined in claim 14 wherein said solution is cardioplegia.

19. The mixing device as defined in claim 18 further comprising an oxygenator disposed intermediate said source of blood and said mixing means.

20. The mixing device as defined in claim 19 further comprising a heat exchanger, disposed intermediate said mixing means and said site of perfusion.

* * * * *